(12) United States Patent
Brink et al.

(10) Patent No.: US 9,024,079 B2
(45) Date of Patent: May 5, 2015

(54) SEPARATION OF ISOMERIC MENTHOL COMPOUNDS

(75) Inventors: Reinhold Brink, Haltern (DE); Lutz Heuer, Dormagen (DE); Sven Kuhlmann, Cologne (DE); Martin Mechelhoff, Cologne (DE); Oliver Pfohl, Hamburg (DE)

(73) Assignee: LANXESS Deutschland GmbH, Cologne, DE (US)

( * ) Notice: Subject to any disclaimer, the term of this patent is extended or adjusted under 35 U.S.C. 154(b) by 0 days.

(21) Appl. No.: 13/594,994

(22) Filed: Aug. 27, 2012
(Under 37 CFR 1.47)

(65) Prior Publication Data
US 2014/0018580 A1    Jan. 16, 2014

Related U.S. Application Data

(63) Continuation of application No. 13/348,008, filed on Jan. 11, 2012, now abandoned.

(51) Int. Cl.
*C07C 29/84* (2006.01)
*C07C 35/12* (2006.01)

(52) U.S. Cl.
CPC ............. *C07C 29/84* (2013.01); *C07C 2101/14* (2013.01)

(58) Field of Classification Search
CPC ........................................................ C07C 29/84
USPC ................................................................ 568/829
See application file for complete search history.

(56) References Cited

U.S. PATENT DOCUMENTS

| 4,874,473 | A | 10/1989 | Arlt et al. |
| 6,429,344 | B1 * | 8/2002 | Langer et al. ................. 568/830 |
| 2008/0283383 | A1 * | 11/2008 | Ruffert et al. ................... 203/29 |
| 2009/0131728 | A1 * | 5/2009 | Shiflett et al. ................. 570/180 |

FOREIGN PATENT DOCUMENTS

| DE | 10136614 A1 | 2/2003 |
| DE | 10154052 A1 | 7/2003 |

OTHER PUBLICATIONS

European Search Report for EP10013850 dated Mar. 24, 2011.

\* cited by examiner

*Primary Examiner* — Jafar Parsa
*Assistant Examiner* — Medhanit Bahta

(57) ABSTRACT

The invention relates to a process for rectificative separation of compositions of matter containing diastereomers of 2-isopropyl-5-methylcyclohexanol by using ionic liquids as extractants.

11 Claims, No Drawings

SEPARATION OF ISOMERIC MENTHOL COMPOUNDS

This application is a continuation of U.S. patent application Ser. No. 13/348,008 filed Jan. 11, 2012, incorporated herein by reference.

The invention relates to a process for rectificative separation of compositions of matter containing diastereomers of 2-isopropyl-5-methylcyclohexanol by using ionic liquids as extractants.

Rectification is widely employed in industry to separate compositions of matter. The difficulty of separating a composition of matter by rectification is indicated by the separation factor α, viz, the ratio of the partition coefficients of the participating components. The farther the separation factor is from unity, the more economical the composition of matter is to separate in general.

Many compositions of matter whose components have only small boiling point differences or even form azeotropes can only be separated with difficulty, if at all, by conventional rectification. This applies for example to the separation of diastereomers of 2-isopropyl-5-methylcyclohexanol (d,l-menthol, d,l-neomenthol, d,l-isomenthol and d,l-neoisomenthol) from compositions of matter containing at least two mutually diastereomeric compounds of 2-isopropyl-5-methylcyclohexanol, as typically formed in the hydrogenation of thymol or subsequent working-up steps. Especially the separation of diastereomers isomenthol and menthol can only be achieved to an inadequate degree and at high energy costs because of the low relative volatility between the two compounds.

In such cases, the composition of matter to be separated is typically admixed with a selective agent known as an entrainer, which selectively interacts with the components of the composition of matter to influence the vapour-liquid phase equilibrium such that better separation factors are obtained than without adding the entrainer.

This typically lowers the energy/cost requirements of the composition of matter used for the separation. Recently, ionic liquids have also been intensively studied for use as entrainers (see also DE 10136614 A, DE 10154052 A and Chem. Ing. Tech. 2003, 75, 1148-1149).

A multiplicity of entrainers for separating stereoisomeric compounds are known from the literature.

U.S. Pat. No. 4,874,473 A describes the use of succinamide and also succinonitrile, glutaronitrile and malononitrile for separating mixtures of isomenthol and menthol.

Against the background of the abovementioned prior art, the problem was that of providing a particularly efficient process for separating the diastereomers of 2-isopropyl-5-methylcyclohexanol.

The invention accordingly provides a process for separating diastereomers of 2-isopropyl-5-methylcyclohexanol from compositions of matter containing at least two mutually diastereomeric compounds of 2-isopropyl-5-methylcyclohexanol via extractive rectification, said process being characterized in that the rectification is performed in the presence of one or more ionic liquids.

Ionic liquids for the purposes of the invention are compounds that have at least one cation or cationic group and at least one anion or anionic group but have no net charge, and have a melting point below 200° C.

Preferred ionic liquids have an organic cation.

Particularly preferred ionic liquids are of formula (I)

[K⁺][A⁻]   (I)

where

[K⁺] represents a cation selected from the group of formulae (IIa) to (IIe)

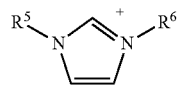   (IIa)

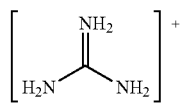   (IIb)

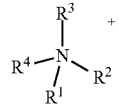   (IIc)

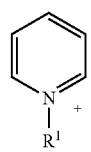   (IId)

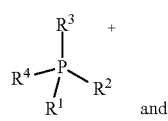   (IIe)

and

[A⁻] represents an anion selected from the group:
hexafluorophosphate, tetrafluoroborate, chloride, bromide, iodide, bis(trifluoromethylsulphonyl)amide and those of formulae (IIIa), (IIIb) and (IIIc)

$$R^7\text{—}SO_3^-$$   (IIIa)

$$^-O(P{=}O)(OR^3)(OR^4)$$   (IIIb)

$$^-O(P{=}O)(R^3)(OR^4)$$   (IIIc)

where, in the formulae (IIa) to (IIe) and also the formulae (IIIa) to (IIIc),
the radicals $R^1$, $R^2$, $R^3$ and $R^4$ each fully independently represent hydrogen, $C_1$-$C_{12}$-alkyl, $C_1$-$C_{12}$-fluoroalkyl, $C_2$-$C_{12}$-alkylene or $C_1$-$C_{12}$-hydroxyalkyl, or
two radicals combine to represent $C_2$-$C_{12}$-alkenylene, where the formulae (IIc) and (IIe) are subject to the proviso that not more than two of $R^1$, $R^2$, $R^3$ and $R^4$ represent hydrogen,
and
the radicals $R^5$ and $R^6$ each fully independently represent hydrogen, hydroxyl, $C_1$-$C_{12}$-alkyl, $C_1$-$C_{12}$-fluoroalkyl or $C_1$-$C_{12}$-hydroxyalkyl,
and
the radical $R^7$ represents a phenyl radical with no, single or multiple substitution by radicals selected from the group $C_1$-$C_{12}$-alkyl, $C_1$-$C_{12}$-fluoroalkyl, fluorine, chlorine, bromine, hydroxyl or $C_1$-$C_{12}$-hydroxyalkyl.

Very particularly preferred ionic liquids are of formula (I) where [K⁺] represents a cation of formula (IIa) or (IIb) and [A⁻] represents hexafluorophosphate or bis(trifluoromethylsulphonyl)amide.

Still further preferred compounds of formula (I) are: 1,3-dihydroxyimidazolium hexafluorophosphate, guanidinium bis(trifluoromethylsulphonyl)amide, 2-hydroxyethylammonium bis(trifluoromethylsulphonyl)amide, imidazolium bis (trifluoromethylsulphonyl)amide, butylammonium triflate, trimethylammonium methanesulphonate, 1,3-dihydroxyimidazolium bis(trifluoromethylsulphonyl)amide, N,N-dimethylethanolammonium bis(trifluoromethylsulphonyl)amide, 1,3-dihydroxy-2-methyl-imidazolium-bis(trifluoromethylsulphonyl)amide, 1-butylimidazolium hexafluorophosphate and guanidinium tris(pentafluoroethyl)trifluorophosphate.

Very particularly preferred compounds of formula (I) are 1,3-dihydroxyimidazolium hexafluorophosphate, guanidinium bis(trifluoromethylsulphonyl)amide, imidazolium bis(trifluoromethylsulphonyl)amide and 1,3-dihydroxyimidazolium bis(trifluoromethylsulphonyl)amide.

$C_1$-$C_{12}$-Alkyl, $C_2$-$C_{12}$-alkylene and $C_2$-$C_{12}$-alkenylene each independently denote respectively a straight-chain, wholly or partly cyclic, branched or unbranched alkyl, alkylene or alkenylene radical having the stated number of carbon atoms, where the radicals mentioned may have no, single or multiple, preferably no or single, further substitution by $C_1$-$C_4$-alkoxy radicals or halogens.

$C_1$-$C_{12}$-Alkyl represents for example methyl, ethyl, 2-methoxyethyl, n-propyl, iso-propyl, n-butyl, sec-butyl and tert-butyl, n-pentyl, 1-methylbutyl, 2-methylbutyl, 3-methylbutyl, neo-pentyl, 1-ethylpropyl, cyclo-hexyl, cyclo-pentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, adamantyl, the isomeric methyls, n-nonyl, n-decyl or n-dodecyl.

$C_1$-$C_4$-Alkoxy represents for example methoxy, ethoxy, 2-methoxyethoxy, n-propoxy, isopropoxy, n-butoxy, sec-butoxy or tert-butoxy.

$C_1$-$C_{12}$-Fluoroalkyl denotes in each case independently a straight-chain, wholly or partly cyclic, branched or unbranched alkyl radical substituted one or more times, preferably completely, by fluorine atoms.

$C_1$-$C_{12}$-Fluoroalkyl represents for example trifluoromethyl, pentafluoroethyl, heptafluoropropyl or perfluorobutyl.

$C_1$-$C_{12}$-Hydroxyalkyl represents a $C_1$-$C_{12}$-alkyl radical as defined above, which is substituted by hydroxyl groups one or more times.

For example, $C_1$-$C_{12}$-hydroxyalkyl represents hydroxymethyl, 2-hydroxyethyl, 2-hydroxypropyl, 3-hydroxypropyl.

$C_2$-$C_{12}$-Alkenyl represents for example vinyl, 1-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl, 1-octenyl or 2-octenyl.

The compounds of formula (I) and their preparation are known in principle and are disclosed for example in Ionic Liquids in Synthesis, 2nd Ed., 2007, Wiley-VCH, Weinheim (eds. Wasserscheid and Welton).

According to the invention, diastereomers of 2-isopropyl-5-methylcyclohexanol are separated from compositions of manner containing at least two mutually diastereomeric compounds of 2-isopropyl-5-methylcyclohexanol via extractive rectification.

This means in the context of the invention that at least one stereoisomer selected from the group d- and l-menthol, d- and l-neomenthol, d- and l-isomenthol and d- and l-neoisomenthol is separated from at least one other relatively diastereomeric isomer selected from the same aforementioned group.

They can be separated off for example l-menthol or d-menthol or any desired mixture of d- and l-menthol from any desired mixture containing one, two, three, four, five or all relatively diastereomeric compounds from the group d- and l-neomenthol, d- and l-isomenthol and d- and l-neoisomenthol;

l-isomenthol or d-isomenthol or any desired mixture of d- and l-isomenthol from any desired mixture containing one, two, three, four, five or all relatively diastereomeric compounds from the group l-menthol and d-menthol, d- and l-neomenthol, and d- and l-neoisomenthol;

l-neomenthol or d-neomenthol or any desired mixture of d- and l-neomenthol from any desired mixture containing one, two, three, four, five or all relatively diastereomeric compounds from the group l-menthol and d-menthol, d- and l-isomenthol, and d- and l-neoisomenthol l-neoisomenthol or d-neoisomenthol or any desired mixture of d- and l-neoisomenthol from any desired mixture containing one, two, three, four, five or all relatively diastereomeric compounds from the group l-menthol and d-menthol, d- and l-isomenthol, and d- and l-neomenthol.

Any desired mixtures of d- and l-stereoisomers also comprise individual racemates or any desired mixtures of racemates.

Preferably l-menthol or d-menthol or any desired mixture of d- and l-menthol are separated from any desired mixture containing one, two, three, four, five or all relatively diastereomeric compounds from the group d- and l-neomenthol, d- and l-isomenthol and d- and l-neoisomenthol, and preferably racemic mixtures of d- and l-menthol are separated from a mixture containing one, two or all racemic mixtures from the group d,l-neomenthol, d,l-isomenthol and d,l-neoisomenthol.

The respective ratio of diastereomers to be separated in the composition of matter used has no in-principle limit.

In one embodiment, the rectification process is performed such that a composition of matter containing essentially the diastereomers of 2-isopropyl-5-methylcyclohexanol which are to be separated is subjected to rectification, the term "essentially" to be understood as meaning that the proportion of components other than the two 2-isopropyl-5-methylcyclohexanol diastereomers to be separated can be either 0% or more than 0% to 30% and preferably more than 0% to 10% by weight and more preferably more than 0% to 2% by weight by way of further compounds.

Suitable compositions of matter can be for example compositions of matter obtained directly as reaction mixture in the hydrogenation of thymol or following a first distillation of the aforementioned reaction mixture as a head, bottom or side stream for example.

In these cases, the aforementioned further compounds are for example unconverted thymol and/or by-products from the hydrogenation of thymol.

One preferred embodiment therefore uses in the process according to the invention compositions of matter containing 60% to 90% by weight and preferably 70% to 85% by weight of menthol (i.e. d-menthol, l-menthol or any desired mixtures thereof including the racemate) and 5% to 35% by weight and preferably 12% to 30% by weight of isomenthol (i.e. d-isomenthol, l-isomenthol or any desired mixtures thereof including the racemate) and either none or more than 0% to 5% by weight of the further 4 stereoisomers of 2-isopropyl-5-methylcyclohexanol, wherein the sum total of the aforementioned stereoisomers of 2-isopropyl-5-methylcyclohexanol in the composition of matter is 97% by weight or more, preferably 98% by weight or more and more preferably 99% by weight or more.

The rectification can utilize any apparatus known to a person skilled in the art as being suitable for rectification such as columns in particular. Such columns comprise simple columns with or without internals, side stream columns, dividing wall columns or thermally coupled distillation columns.

Preferably, the composition of matter used in the extractive rectification is initially adjusted to or has a temperature which, depending on the choice of pressure in the rectification, is between 20 and 180° C. and preferably between 80 and 160° C. In one preferred embodiment, the temperature at the bottom of the rectification column is 180° C. or less and more preferably 160° C. or less.

In one preferred embodiment, the pressure at the top of the column is generally, depending on the mixture to be separated, in the range for example from 5 to 500 hPa and preferably from 5 to 200 hPa.

The pressure difference between the bottom of the column and the top of the column can be for example in the range from 0 to 200 hPa and preferably in the range from 1 to 100 hPa.

The number of theoretical plates can be for example in the range from 5 to 1000 and preferably in the range from 30 to 300.

The weight ratio of runback to distillate taking off can be for example in the range from 0.5:1 to 20:1 more preferably in the range from 2:1 to 8:1.

The weight ratio of ionic liquids, or of compounds of formulae (I), to the feed to the rectification column of composition of matter to be separated can be for example in the range from 2:1 to 40:1 and preferably in the range from 2:1 to 8:1.

The process according to the invention can be carried out batchwise or continuously, preferably continuously.

Especially in the case of the continuous process, the composition of matter to be separated and the ionic liquid can be fed in a conventional manner, and preferably the ionic liquid is fed into the column above the point of feed for the composition of matter to be separated.

The rectification typically provides at least two product streams in that, for example, one 2-isopropyl-5-methylcyclohexanol diastereomer or a pair of 2-isopropyl-5-methylcyclohexanol diastereomers can be taken off as product stream overhead or in a side stream and the further diastereomer(s) or pair(s) of diastereomers with the ionic liquid(s) as bottom stream.

In one preferred embodiment of the process according to the invention, the ionic liquid is recovered and reused for separation.

The ionic liquids or compounds of formula (I) are recovered for example by distillative separation from the bottom stream. The distillative separation is preferably carried out in two separation stages without reflux. The first separation stage is operated at a pressure in the range from 2 to 200 hPa and preferably 5 to 50 hPa to very substantially remove the 2-isopropyl-5-methylcyclohexanol diastereomer(s) or pair(s) of 2-isopropyl-5-methylcyclohexanol diastereomers in the bottom stream, the expression "very substantially" here to be understood as meaning a more than 90% removal and preferably a more than 95% removal. A second separation stage thereafter effects a further removal at a lower pressure than in the first separation stage, ranging for example from 1 to 20 hPa and preferably from 1 to 5 hPa. Product vapours are advantageously condensed after decompression to, for example, 5-200 hPa and preferably 5-50 hPa.

The particular advantage of the process according to the invention is that mixtures of diastereomeric 2-isopropyl-5-methylcyclohexanols can be efficiently separated to obtain diastereomers or pairs of diastereomers having high purities.

The invention therefore further provides for the use of ionic liquids, especially of compounds of formula (I), for separating diastereomers of 2-isopropyl-5-methylcyclohexanol.

The invention provides for a distinct lowering of specific energy requirements and for an appreciable reduction in the dimensions of the separation apparatus used, i.e. in the apparatus volume needed per separation stage required.

EXAMPLES

Separation of Diastereomeric Mixtures

The following coefficients of activity factors were determined using the COSMO-RS program from COSMOlogic GmbH & Co KG assuming infinite dilution and a temperature of 130° C.:

| Entrainer | $\gamma$ (menthol)/ $\gamma$ (isomenthol) |
|---|---|
| 1,3-dihydroxyimidazolium hexafluorophosphate | 1.25 |
| guanidinium bis(trifluoromethylsulphonyl)amide | 1.19 |
| 2-hydroxyethylammonium bis(trifluoromethylsulphonyl)amide | 1.19 |
| imidazolium bis(trifluoromethylsulphonyl)amide | 1.18 |
| butylammonium triflate | 1.17 |
| trimethylammonium methanesulphonate | 1.17 |
| 1,3-dihydroxyimidazolium bis(trifluoromethylsulphonyl)amide | 1.17 |
| N,N-dimethylethanolammonium bis(trifluoromethylsulphonyl)amide | 1.16 |
| 1,3-dihydroxy-2-methylimidazolium bis(trifluoromethylsulphonyl)amide | 1.15 |
| 1-butylimidazolium hexafluorophosphate | 1.15 |
| guanidinium tris(pentafluoroethyl)trifluorophosphate | 1.15 |

The tests showed that the process according to the invention is distinctly superior to the prior art.

Distillation Example

An extraction column having 220 theoretical plates was supplied with the composition of matter to be separated, consisting of 84% by weight of d,l-menthol and 16% by weight of d,l-isomenthol, at a temperature of 140° C. and the extractant 1,3-dihydroxyimidazolium hexafluorophosphate at a temperature of 140° C. The entrainer was fed into the column above the aforementioned composition of matter. The ratio of menthol to entrainer was 1:8.

The pressure was 80 hPa at the top of the column and 160 hPa at the bottom of the column. The extractant left the bottom of the column at a temperature of about 150° C. The bottom stream contained more than 99% by weight of the isomenthol used and less than 1% by weight of the menthol used. A high-purity menthol having a content of more than 99% by weight was taken off from the column as overhead stream, with the reflux ratio (runback quantity/distillate) being 4:1.

The invention claimed is:

1. A process for separating diastereomers, the process comprising:
   introducing into an extractive rectification column,
   a composition of matter containing a mixture of at least two diastereomers of 2-isopropyl-5-methylcyclohexanol, and
   one or more ionic liquids selected to enhance the boiling point difference between at least one diastereomer of the mixture and at least one other diastereomer of the mixture, wherein the one or more ionic liquids are selected from the group consisting of 1,3-dihydroxyimidazolium hexfluorophosphate, guanidinium bis (trifluoromethylsulphonyl)amide, 2-hydroxyethylammonium bis(trifluoromethylsulphonyl)amide, imidazolium bis(trifluoromethylsulphonyl)amide, butylammonium triflate, trimethylammonium methanesulphonate, 1,3-dihydroxyimidazolium bis(trifluoromethylsulphonyl)amide, N,N-dimethylethanolammonium bis(trifluoromethylsulphonyl)amide, 1,3-dihydroxy-2-methyl-imidazolium-bis(trifluoromethylsulphonyl)amide, 1-butylimidazolium hexafluorophosphate, guanidinium tris(pentafluoroethyl)trifluorophosphate and any mixtures thereof, and performing extractive rectification on the composition of matter in the presence of the one or more ionic liquids to separate the at least one diastereomer of 2-isopropyl-5-methylcyclohexanol from the at least one other diastereomer of 2-isopropyl-5-methylcyclohexanol.

2. The process according to claim 1, wherein the process is a process for separating diastereomers of:
- l-menthol or d-menthol or any desired mixture of d- and l-menthol from any desired mixture containing one, two, three, four, five or all diastereomers from the group d- and l-neomenthol, d- and l-isomenthol and d- and l-neoisomenthol,
- l-isomenthol or d-isomenthol or any desired mixture of d- and l-isomenthol from any desired mixture containing one, two, three, four, five or all diastereomers from the group l-menthol and d-menthol, d- and l-neomenthol, and d- and l-neoisomenthol;
- l-neomenthol or d-neomenthol or any desired mixture of d- and l-neomenthol from any desired mixture containing one, two, three, four, five or all diastereomers from the group l-menthol and d-menthol, d- and l-isomenthol, and d- and l-neoisomenthol; and/or
- l-neoisomenthol or d-neoisomenthol or any desired mixture of d- and l-neoisomenthol from any desired mixture containing one, two, three, four, five or all diastereomers from the group l-menthol and d-menthol, d- and l-isomenthol, and d- and l-neomenthol.

3. The process according to claim 1, wherein l-menthol or d-menthol or any desired mixture of d- and l-menthol are separated from any desired mixture containing one, two, three, four, five or all diastereomers from the group d- and l-neomenthol, d- and l-isomenthol and d- and l-neoisomenthol.

4. The process according to claim 1, wherein the composition of matter is obtained directly as a reaction mixture in the hydrogenation of thymol or following a first distillation of the aforementioned reaction mixture.

5. The process according to claim 1, wherein the composition of matter contains
- 60% to 90% by weight of d-menthol, l-menthol or any desired mixtures thereof, including the racemate, and
- 5% to 35% by weight of d-isomenthol, l-isomenthol or any desired mixtures thereof including the racemate, wherein the sum total of the aforementioned stereoisomers of 2-isopropyl-5-methylcyclohexanol in the composition of matter is 97% by weight or more.

6. The process according to claim 1, wherein the extractive rectification comprises use of a rectification column and in which a weight ratio of residue to distillate is in the range from 0.5:1 to 20:1.

7. The process according to claim 1, wherein the weight ratio of ionic liquids to the amount of composition of matter is in the range from 2:1 to 40:1.

8. The process according to claim 1, wherein the ionic liquid is recovered and reused for separation.

9. The process according to claim 1, wherein the process is performed continuously.

10. The process according to claim 1, wherein the extractive rectification feeding the ionic liquid into the extractive rectification column above the point of feed for the composition of matter to be separated.

11. The process according to claim 5, wherein the composition of matter contains 4 stereoisomers of 2-isopropyl-5-methylcyclohexanol.

\* \* \* \* \*